United States Patent [19]

Barger et al.

[11] Patent Number: 5,191,141
[45] Date of Patent: Mar. 2, 1993

[54] PROCESS FOR CONVERTING METHANOL TO OLEFINS USING AN IMPROVED METAL ALUMINOPHOSPHATE CATALYST

[75] Inventors: Paul T. Barger, Arlington Heights, Ill.; Stephen T. Wilson, Shrub Oak, N.Y.; Jennifer S. Holmgren, Bloomingdale, Ill.

[73] Assignee: UOP, Des Plaines, Ill.

[21] Appl. No.: 862,018

[22] Filed: Apr. 1, 1992

Related U.S. Application Data

[63] Continuation-in-part of Ser. No. 790,908, Nov. 13, 1991, Pat. No. 5,126,308.

[51] Int. Cl.$^5$ ................................................ C07C 1/24
[52] U.S. Cl. ...................................... 585/640; 502/214
[58] Field of Search .................... 585/639, 640; 502/214

[56] References Cited

U.S. PATENT DOCUMENTS

| | | | |
|---|---|---|---|
| 4,238,631 | 12/1980 | Daviduk et al. | 585/639 |
| 4,310,440 | 1/1982 | Wilson et al. | 252/435 |
| 4,328,384 | 5/1982 | Daviduk et al. | 585/639 |
| 4,423,274 | 12/1983 | Daviduk et al. | 585/640 |
| 4,440,871 | 4/1984 | Lok et al. | 502/214 |
| 4,499,327 | 12/1985 | Kaiser | 585/640 |
| 4,554,143 | 11/1985 | Messina et al. | 423/306 |
| 4,612,406 | 9/1986 | Long et al. | 585/640 |
| 4,677,243 | 6/1987 | Kaiser | 585/640 |
| 4,752,651 | 6/1988 | Kaiser | 585/640 |
| 4,793,984 | 12/1988 | Lok et al. | 423/306 |
| 4,814,541 | 3/1989 | Lewis | 585/733 |
| 4,826,804 | 5/1989 | Shamshoum | 502/214 |
| 4,849,575 | 7/1989 | Lewis | 585/640 |
| 4,853,197 | 8/1989 | Wilson et al. | 423/306 |
| 5,095,163 | 3/1992 | Barger | 585/640 |
| 5,126,308 | 6/1992 | Barger et al. | 502/214 |

OTHER PUBLICATIONS

Inui et al., Applied Catalysis, 58 (1990) 155-163.

Primary Examiner—Anthony McFarlane
Attorney, Agent, or Firm—Thomas K. McBride; Eugene I. Snyder; Frank S. Molinaro

[57] ABSTRACT

This invention relates to an improved process for converting methanol to light olefins using an ELAPO catalyst. The catalyst comprises a metal aluminophosphate molecular sieve having the empirical formula $(EL_x Al_y P_z)O_2$ where EL is a metal and x,y and z are mole fractions of EL, Al and P respectively. Preferred metals are silicon, magnesium and cobalt, with silicon especially preferred. The molecular sieve catalyst is composed of particles at least 50% of which have a particle size less than 1.0 μm and no more than 10% of the particles have a particle size greater than 2.0 μm. It is also preferred that the metal content (x) be from about 0.005 and 0.05 mole fraction.

10 Claims, No Drawings

PROCESS FOR CONVERTING METHANOL TO OLEFINS USING AN IMPROVED METAL ALUMINOPHOSPHATE CATALYST

CROSS REFERENCE TO RELATED APPLICATION

This application is a continuation-in-part of prior copending application U.S. Ser. No. 07/790,908 filed on Nov. 13, 1991, now U.S. Pat. No. 5,126,308.

FIELD OF THE INVENTION

This invention relates to a process using a novel catalyst to convert methanol to light olefins. The catalyst comprises a crystalline metal aluminophosphate molecular sieve having the formula $(EL_xAl_yP_z)O_2$ and characterized in that at least 50% of the catalyst particles have a particle size smaller than 1.0 μm and no more than 10% of the particles have particle sizes greater than 2.0 μm.

BACKGROUND OF THE INVENTION

The limited supply and increasing cost of crude oil has prompted the search for alternative processes for producing hydrocarbon products. One such process is the conversion of methanol to hydrocarbons and especially light olefins (by light is meant $C_2$ to $C_4$ olefins). The interest in the methanol to olefin process is based on the fact that methanol can be obtained from coal or natural gas by the production of synthesis gas which is then processed to produce methanol.

Processes for converting methanol to light olefins are well known in the art. Initially aluminosilicates or zeolites were used as the catalysts necessary to carry out the conversion. For example, see U.S. Pat. Nos. 4,238,631; 4,328,384, 4,423,274. These patents further disclose the deposition of coke onto the zeolites in order to increase selectivity to light olefins and minimize the formation of $C_5+$ byproducts. The effect of the coke is to reduce the pore diameter of the zeolite.

The prior art also discloses that silicoaluminophosphates (SAPOs) can be used to catalyze the methanol to olefin process. Thus, U.S. Pat. No. 4,499,327 discloses that many of the SAPO family of molecular sieves can be used to convert methanol to olefins. The '327 patent also discloses that preferred SAPOs are those that have pores large enough to adsorb xenon (kinetic diameter of 4.0 Å) but small enough to exclude isobutane (kinetic diameter of 5.0 Å). A particularly preferred SAPO is SAPO-34.

U.S. Pat. No. 4,752,651 discloses the use of nonzeolitic molecular sieves (NZMS) including ELAPOs and MeAPO molecular sieves to catalyze the methanol to olefin reaction.

Finally, Inui et al. in Applied Catalysis, 58, (1990) 155–163 prepared SAPO-34 materials by what they call the rapid crystallization method. One result of using this procedure is that the SAPO product had crystallites in the range of 0.5 to 2 microns. However, the researchers do not state what the distribution of crystallites is throughout the range. There is also no recognition that smaller crystallites affect catalyst activity or life.

Applicants have found that molecular sieves having the empirical formula $(EL_xAl_yP_z)O_2$ (hereinafter ELAPO) where EL is a metal selected from the group consisting of silicon, magnesium, zinc, iron, cobalt, nickel, manganese, chromium and mixtures thereof and x, y and z are the mole fractions of EL, Al and P respectively, and having a small particle size, have a considerably longer life and increased selectivity versus previous catalysts. Specifically the ELAPOs of the instant invention are characterized in that at least 50% of the molecular sieve particles have a particle size less than 1.0 μm and no more than 10% of the particles have a particle size greater than 2.0 μm. Applicants have also found that restricting the total metal (EL) content from about 0.005 to about 0.05 mole fraction further improves the catalytic performance of the ELAPO molecular sieve. There is no indication in the art that reducing the particle size and/or the total metal content of an ELAPO molecular sieve would increase its catalytic performance.

SUMMARY OF THE INVENTION

As stated, this invention relates to a process for converting methanol to light olefins using an ELAPO catalyst. Accordingly, one embodiment of the invention is a process for converting methanol to light olefins comprising contacting the methanol with a catalyst comprising a crystalline metal aluminophosphate at conversion conditions, the metal aluminophosphate characterized in that it has an empirical composition on an anhydrous basis expressed by the formula $$(EL_xAl_yP_z)O_2$$

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and $x+y+z=1$, the metal aluminophosphate characterized in that it is composed of particles at least 50% of which have a particle size less than 1.0 μm and no more than 10% of the particles have a particle size greater than 2.0 μm.

This and other embodiments will become more apparent in the following detailed description.

DETAILED DESCRIPTION OF THE INVENTION

As already stated the instant invention relates to a process for converting methanol to light olefins using an ELAPO catalyst. As will be used herein, light olefins will mean $C_2$ to $C_4$ olefins. ELAPOs are molecular sieves which have a three-dimensional microporous framework structure of $AlO_2$, $PO_2$ and $ELO_2$ tetrahedral units. Generally the ELAPOs have the empirical formula:

$$(EL_xAl_yP_z)O_2$$

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and $x+y+z=1$. When EL is a mixture of metals, x represents the total amount of the metal mixture present. Preferred metals (EL) are silicon, magnesium and cobalt with silicon being especially preferred.

The preparation of various ELAPOs are well known in the art and may be found in U.S. Pat. Nos.: 4,554,143 (FeAPO); 4,440,871 (SAPO); 4,853,197 (MAPO, MnAPO, ZnAPO, CoAPO); 4,793,984 (CAPO), 4,752,651 and 4,310,440, all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon a preferred source is fumed, colloidal or precipated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

The reaction mixture is placed in a sealed pressure vessel, optionally lined with an inert plastic material such as polytetrafluoroethylene and heated preferably under autogenous pressure at a temperature between about 50° C. and 250° C. and preferably between about 100° C. and 200° C. for a time sufficient to produce crystals of the ELAPO molecular sieve. Typically the time varies from about 2 hours to about 30 days and preferably from about 4 hours to about 20 days. The desired product is recovered by any convenient method such as centrifugation or filtration.

Applicants have discovered that the particle size of the ELAPO molecular sieve can be reduced by stirring the reaction mixture at high speeds (see examples) and by using TEAOH as the templating agent. Additionally, as the amount of the M metal is lowered, the particle size is also reduced. By employing these modifications, applicants have been able to obtain ELAPO molecular sieves composed of particles at least 50% of which have a particle size less than 1.0 $\mu$m and no more than 10% of the ELAPO particles have a particle size greater than 2.0 $\mu$m.

As stated in the examples, the particle size was determined by the technique of gravitational sedimentation. Several samples were also analyzed by scanning electron microscopy (SEM) which confirmed the sedimentation results and showed that the particle size is the same as the crystallite size.

The ELAPOs which are synthesized using the process described above will usually contain some of the organic templating agent in its pores. In order for the ELAPOs to be active catalysts, the templating agent in the pores must be removed by heating the ELAPO powder in an oxygen containing atmosphere at a temperature of about 200° to about 700° C. until the template is removed, usually a few hours.

A preferred embodiment of the invention is one in which the metal (EL) content varies from about 0.005 to about 0.05 mole fraction. If EL is more than one metal then the total concentration of all the metals is between about 0.005 and 0.05 mole fraction. An especially preferred embodiment is one in which EL is silicon (usually referred to as SAPO). The SAPOs which can be used in the instant invention are any of those described in U.S. Pat. No. 4,440,871. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å.

The ELAPO molecular sieve of this invention may be used alone or they may be mixed with a binder and formed into shapes such as extrudates, pills, spheres, etc. Any inorganic oxide well known in the art may be used as a binder. Examples of the binders which can be used include alumina, silica, aluminum-phosphate, silica-alumina, etc. When a binder is used, the amount of ELAPO which is contained in the final product ranges from 10 to 90 weight percent and preferably from 30 to 70 weight percent.

The conversion of methanol to olefins is effected by contacting the methanol with the SAPO catalyst at conversion conditions, thereby forming the desired olefins. The methanol can be in the liquid or vapor phase with the vapor phase being preferred. Contacting the methanol with the SAPO catalyst can be done in a continuous mode or a batch mode with a continuous mode being preferred. The amount of time that the methanol is in contact with the SAPO catalyst must be sufficient to convert the methanol to the desired light olefin products. When the process is carried out in a batch process, the contact time varies from about 0.001 hrs. to about 1 hr. and preferably from about 0.01 hr. to about 1.0 hr. The longer contact times are used at lower temperatures while shorter times are used at higher temperatures. Further, when the process is carried out in a continuous mode, the Weight Hourly Sapce Velocity (WHSV) based on methanol can vary from about 1 $hr^{-1}$ to about 1000 $hr^{-1}$ and preferably from about 1 $hr^{-1}$ to about 100 $hr^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 450° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e.g., methane, aromatic hydrocarbons, e.g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the ELAPO catalyst. When multiple reaction zones are used, one or more ELAPO catalyst may be used in series to produce the desired product mixture. Instead of a fixed bed, a dynamic bed system, e.g., fluidized or moving, may be used. Such a dynamic system would facilitate any regeneration of the ELAPO catalyst that may be required. If regeneration is required, the ELAPO catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims.

EXAMPLES

The x-ray diffraction of the samples prepared in the following examples were obtained using standard x-ray powder diffraction techniques on a Siemens D-500 x-ray powder diffractometer. The radiation source was a high-intensity, copper target, x-ray tube operated at 50 Kv and 24 mA.

Particle size analysis was based on the technique of gravitational sedimentation using a Micromeritics Sedigraph 5100. This instrument uses the attenuation of soft x-rays to monitor particle concentration as a function of depth in the suspension. At the start of the analysis, the sample cell containing a dilute slurry of the sample particles is positioned relative to the stationary x-ray detector at a depth sufficient to include the largest particles expected in the sample. The cell is then moved downward through the x-ray beam at a programmed rate, so that the time and depth in the suspension define a given particle diameter. The attenuation of the x-ray beam monitors the concentration of the disperse phase having this diameter. The results of analysis are obtained as a graph of the cumulative mass percent undersize as a function of equivalent spherical diameter. The overall size range that can be investigated by the Sedigraph is 0.1–100 μm, depending upon particle specific gravity. For the examples to follow, 1.4 grams of solid was suspended in 25 mL distilled water.

EXAMPLE 1

16940 lbs. of water, 7700 lbs. of 75 wt % orthophosphoric acid, and 1200 lbs. of silica (HiSil ™ 250) were added to tank A and mixed until homogeneous. 5400 lbs. of tetraethylammonium hydroxide (TEAOH, 40 wt % aqueous) were added to the mixture and blended in, followed by 5940 lbs. of di-n-propylamine (nPr$_2$NH). Finally, 4000 lbs. of alumina (Kaiser Versal ™ 250) was added and the mixture was stirred until homogeneous. The resulting reaction mixture had an elemental composition in molar oxide ratios of:

2.0nPr$_2$NH:0.5TEAOH:0.6SiO$_2$:1.0Al$_2$O$_3$:1.0P$_2$O$_5$:50H$_2$O.

A 5 gal. aliquot of this mixture was crystallized in a 5 gallon Chemineer pressure reactor by heating for 17 hours at 175° C. The reaction mixture was cooled to ambient temperature and the solid product recovered and washed by centrifugation. The product had a median particle diameter, expressed as a mass distribution, of 0.90 micrometers. 90% of the total sample mass had a median particle diameter <3.0 micrometers and 10% had a median particle size <0.5 micrometers. This sample had an x-ray diffraction pattern characteristic of SAPO-34.

The product composition, expressed as weight percents, was:

| | |
|---|---|
| Al$_2$O$_3$ | 32.30 |
| P$_2$O$_5$ | 34.40 |
| SiO$_2$ | 10.80 |
| CARBON | 10.40 |
| NITROGEN | 1.40 |
| LOSS ON IGNITION | 21.8 |

The sample was identified as sample A.

EXAMPLE 2

99.8 grams of 85% orthophosphoric acid was combined with 95.5 grams of distilled water. 33.2 grams of a silica sol (Ludox ™ LS, 30 wt % SiO$_2$) was blended in, followed by 159.1 grams of a 40 wt % aqueous solution of tetraethylammonium hydroxide (TEAOH). Finally, 62.4 grams of a pseudo-boehmite form of precipitated alumina (Versal ™ 250, 70.6 wt % Al$_2$O$_3$, 29.4 wt % H$_2$O) was added and blended in. The resulting reaction mixture had an elemental composition in molar oxide ratios of:

1.00TEAOH:0.40SiO$_2$:100Al$_2$O$_3$:1.00P$_2$O$_5$:35H$_2$O.

The mixture was placed in a 600 mL stainless steel pressure reactor equipped with a turbine stirrer. It was stirred at 550 rpm and heated to 150° C. over a 5 hour period, then maintained at 150° C. for 72 hours to crystallize. the reaction mixture was cooled to ambient temperature and the solid product recovered and washed by centrifugation. The product had a median particle diameter, expressed as a mass distribution, of 0.71 micrometers. 90% of the total sample mass had a median particle diameter <1.2 micrometers. This product had an x-ray diffraction pattern characteristic of SAPO-34.

The product composition, expressed as weight percents, was:

| | |
|---|---|
| Al$_2$O$_3$ | 33.10 |
| P$_2$O$_5$ | 41.00 |
| SiO$_2$ | 6.90 |
| CARBON | 10.70 |
| NITROGEN | 1.50 |
| LOSS ON IGNITION | 19.0 |

This sample was identified as sample B.

EXAMPLE 3

159.0 grams of a 40 wt % aqueous solution of tetraethylammonium hydroxide (TEAOH) was diluted with 152.6 grams of distilled water. 33.2 grams of a silica sol (Ludox ™ LS, 30 wt % SiO$_2$) was blended in. The mixture was placed in a 600 mL stainless steel pressure reactor equipped with a turbine stirrer. Finally, 105.3 grams of aluminophosphate spheres prepared according to U.S. Pat. No. 4,629,717 (incorporated by reference) and having an Al/P of 1.0 was added. The resulting reaction mixture had an elemental composition in molar oxide ratios of:

1.00TEAOH:0.40SiO$_2$:1.00Al$_2$O$_3$:1.00P$_2$O$_5$:35H$_2$O.

The mixture was stirred at 550 rpm and heated to 150° C. over a 5 hour period, then maintained at 150° C. for 72 hours to crystallize. The reaction mixture was cooled to ambient temperature and the solid product recovered and washed by centrifugation. The product had a median particle diameter, expressed as a mass distribution, of 1.42 micrometers. 90% of the total sample mass had a median particle diameter <2.4 micrometers. This product had an x-ray diffraction pattern characteristic of SAPO-34.

The product composition, expressed as weight percents, was:

| | |
|---|---|
| Al$_2$O$_3$ | 33.50 |

-continued

| | |
|---|---|
| P₂O₅ | 40.50 |
| SiO₂ | 7.25 |
| CARBON | 10.80 |
| NITROGEN | 1.50 |
| LOSS ON IGNITION | 18.6 |

This sample was identified as sample C.

EXAMPLE 4

101.1 grams of 85% orthophosphoric acid was combined with 110.4 grams of distilled water. 159.1 grams of a 40 wt % aqueous solution of tetraethylammonium hydroxide (TEAOH) was added to give a solution. With continuous stirring 8.4 grams of a silica sol (Ludox TM LS, 30 wt % SiO₂) was blended in, followed by 68.7 grams of a pseudo-boehmite form of precipitated alumina (Versal TM 250: 70.6 wt % Al₂O₃, 29.4 wt % H₂O). The resulting reaction mixture had an elemental composition in molar oxide ratios of:

$$1.00TEAOH:0.10SiO_2:1.00Al_2O_3:1.00P_2O_5:35H_2O$$

The mixture was placed in a 600 mL stainless steel pressure reactor equipped with a turbine stirrer. It was stirred at 550 rpm and heated to 150° C. over a 5 hour period, then maintained at 150° C. for 72 hours to crystallize. The reaction mixture was cooled to ambient temperature and the solid product recovered and washed by centrifugation. The product had a median particle diameter, expressed as a mass distribution, of 0.94 micrometers. 90% of the total sample mass had a median particle diameter < 1.9 micrometers. This product had an x-ray diffraction pattern characteristic of SAPO-34.

The product composition, expressed as weight percents, was:

| | |
|---|---|
| Al₂O₃ | 34.50 |
| P₂O₅ | 44.30 |
| SiO₂ | 2.52 |
| CARBON | 10.32 |
| NITROGEN | 1.36 |
| LOSS ON IGNITION | 19.2 |

This sample was identified as sample D.

EXAMPLE 5

101.4 grams of 85% orthophosphoric acid was combined with 113.6 grams of distilled water. 161.8 grams of a 40 wt % aqueous solution of tetraethylammonium hydroxide (TEAOH) was added to give a solution. With continuous stirring 4.2 grams of a silica sol (Ludox TM LS, 30 wt % SiO₂) was blended in, followed by 68.9 grams of a pseudo-boehmite form of precipitated alumina (Versal TM 250, 70.6 wt % Al₂O₃, 29.4 wt % H₂O). The resulting reaction mixture had an elemental composition in molar oxide ratios of:

$$1.00TEAOH:0.05SiO_2:1.00Al_2O_3:1.00P_2O_5:35H_2O$$

The mixture was placed in a 600 mL stainless steel pressure reactor equipped with a turbine stirrer. It was stirred at 550 rpm and heated to 175° C. over a 5 hour period, then maintained at 175° C. for 72 hours to crystallize. The reaction mixture was cooled to ambient temperature and the solid product recovered and washed by centrifugation. The product had a median particle diameter, expressed as a mass distribution, of 0.61 micrometers. 90% of the total sample mass had a median particle diameter < 1.2 micrometers. This product had an x-ray diffraction pattern characteristic of SAPO-34.

The product composition, expressed as weight percents, was:

| | |
|---|---|
| Al₂O₃ | 34.50 |
| P₂O₅ | 45.50 |
| SiO₂ | 1.29 |
| CARBON | 10.31 |
| NITROGEN | 1.41 |
| LOSS ON IGNITION | 18.9 |

This sample was identified as sample E.

EXAMPLE 6

The catalysts prepared in Examples 1-5 were evaluated for the conversion of methanol to light olefins in a fixed bed pilot plant. A 10 gram sample in the form of 20-40 mesh agglomerates was used for the testing. Before testing, each sample was calcined in air in a muffle oven at 650° C. for 2 hours and then pre-treated in situ by heating to 400° C. for 1 hour under hydrogen. The pretreated sample was now contacted with a feed consisting of methanol, $H_2O$ and $H_2$ in a 1/4.6/5.3 molar ratio at 400° C., 5 psig and 1 $hr^{-1}$ MeOH WHSV. The composition of the effluent was measured by an on-line GC after 45 minutes on stream to determine initial conversion and selectivities. To determine catalyst life the runs were continued until methanol or dimethylether was observed in the reactor effluent. The results are tabulated in Table 1. This data shows that improved catalyst performance, in terms of reduced $C_3$ by-product formation and/or increased catalyst life, is obtained by the use of a catalyst having an average particle size of less than 1.0 μm and/or less than 0.05 moles fraction Si. Superior performance is obtained with catalysts that combine these two properties.

TABLE 1

| Catalyst | Particle Size (μm) 50%* | 90%** | Si (mole fract.) | Initial Performance Conv. | $C_2^=+C_2^=$ Sel. | $C_3$ Sel. | Catalyst Life (hr) |
|---|---|---|---|---|---|---|---|
| A | 1.2 | | 0.14 | 100 | 70.6 | 7.3 | 15 |
| B | 0.7 | 1.3 | 0.09 | 100 | 73.2 | 3.5 | 25 |
| C | 1.4 | 2.5 | 0.09 | 100 | 75.3 | 2.9 | 14 |
| D | 0.9 | 2.0 | 0.03 | 100 | 73.9 | 1.1 | 36 |
| E | 0.6 | 1.2 | 0.016 | 100 | 72.9 | 0.7 | 33 |

*50% of the particles are smaller than the listed values.
**90% of the particles are smaller than the listed values.

We claim as our invention:

1. A process for converting methanol to light olefins comprising contacting the methanol with a catalyst comprising a crystalline metal aluminophosphate at conversion conditions, the metal aluminophosphate characterized in that it has an empirical composition on an anhydrous basis expressed by the formula $$(EL_xAl_yP_z)O_2$$

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and $x+y+z=1$, the metal aluminophosphate characterized in that it is composed of particles at least 50% of which have a particle size less than 1.0 μm and no more than 10% of the particles have a particle size greater than 2.0 μm.

2. The process of claim 1 where the metal aluminophosphate has a metal content from about 0.005 to about 0.05 mole fraction.

3. The process of claim 1 where EL in the metal aluminophosphate is selected from the group consisting of silicon, magnesium, cobalt and mixtures thereof.

4. The process of claim 3 where the metal aluminophosphate is a silicon aluminophosphate (SAPO).

5. The process of claim 4 where the metal aluminophosphate has the crystal structure of SAPO-34.

6. The process of claim 1 where the catalyst comprises a metal aluminophosphate and an inorganic oxide binder.

7. The process of claim 6 where the binder is selected from the group consisting of alumina, silica, aluminum phosphate, silica-alumina and mixtures thereof.

8. The process of claim 6 where the metal aluminophosphate is present in an amount from about 10 to about 90 weight percent of the catalyst.

9. The process of claim 8 where the metal aluminophosphate is present in an amount from about 30 to about 70 weight percent of the catalyst.

10. The process of claim 1 where the conversion conditions are a temperature of about 300° to about 600° C., a pressure of about 0 kPa to about 17244 kPa (250 psig) and a weight hourly space velocity of about 1 to about 1000 $hr^{-1}$.

* * * * *